United States Patent [19]

Ramachandran et al.

[11] Patent Number: 5,365,011
[45] Date of Patent: Nov. 15, 1994

[54] METHOD OF PRODUCING UNSATURATED HYDROCARBONS AND SEPARATING THE SAME FROM SATURATED HYDROCARBONS

[75] Inventors: Ramakrishnan Ramachandran, Allendale; Loc H. Dao, Bound Brook, both of N.J.

[73] Assignee: The BOC Group, Inc., New Providence, N.J.

[21] Appl. No.: 54,641

[22] Filed: May 5, 1993

Related U.S. Application Data

[63] Continuation-in-part of Ser. No. 891,501, May 29, 1992, abandoned.

[51] Int. Cl.⁵ .................................................. C07C 7/13
[52] U.S. Cl. ............................. 585/829; 585/654; 585/655; 585/820
[58] Field of Search ............... 585/655, 809, 820, 829, 585/654

[56] References Cited

U.S. PATENT DOCUMENTS

| | | | |
|---|---|---|---|
| 3,903,191 | 9/1975 | Pollitzer | 585/655 |
| 4,954,242 | 9/1990 | Gruia | 208/99 |
| 5,008,412 | 4/1991 | Ramachandran et al. | 585/654 |
| 5,146,037 | 9/1992 | Zarchy et al. | 585/734 |
| 5,177,293 | 1/1993 | Mitariten et al. | 585/655 |

FOREIGN PATENT DOCUMENTS 150885 9/1981 Germany .

OTHER PUBLICATIONS

Union Carbide Molecular Sieves Hydrocarbon Material Data Sheets, Union Carbide Corp., Mol. Sieve Dept. (No date available).

*Primary Examiner*—Anthony McFarlane
*Attorney, Agent, or Firm*—Coleman R. Reap; Larry R. Cassett

[57] ABSTRACT

Method of separating a gaseous alkene from a gaseous alkane by a pressure swing adsorption process unit alone or in combination with the distillation column wherein the alkene is preferentially adsorbed onto a bed of 4A zeolite at a temperature of about 50° to about 200° C.

22 Claims, 3 Drawing Sheets

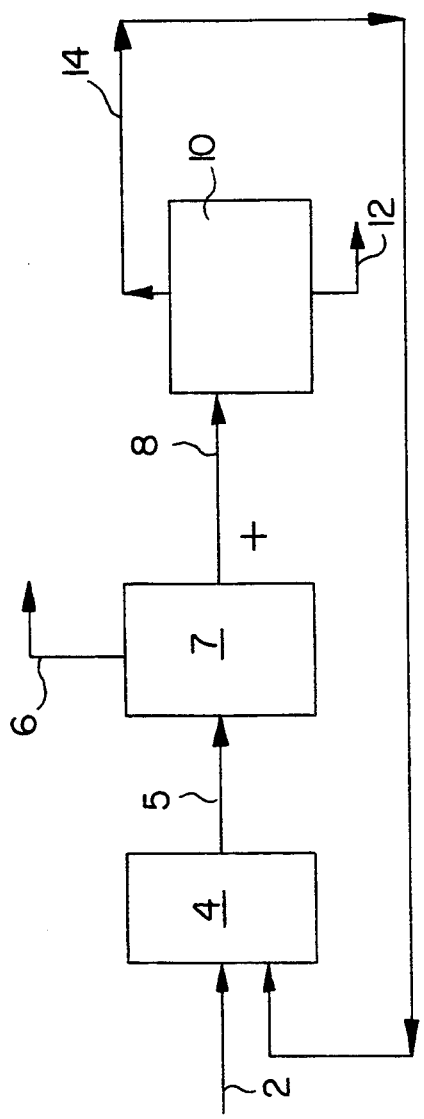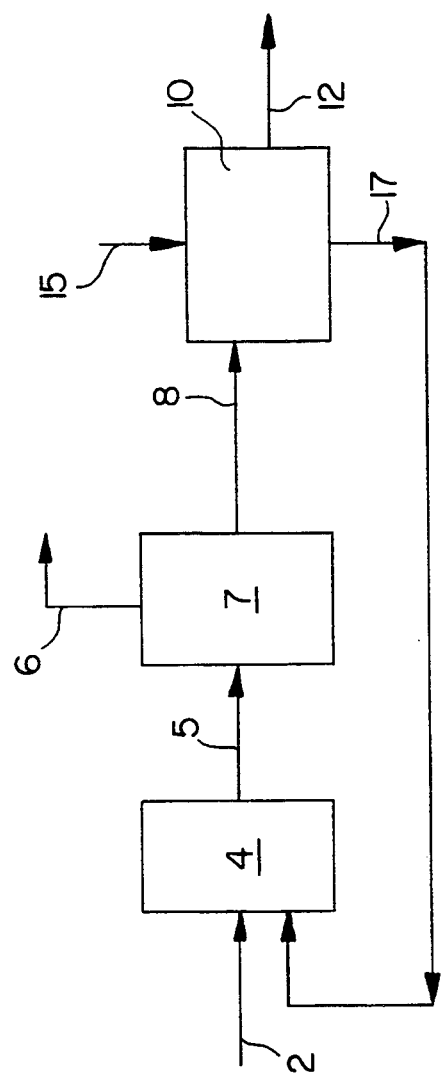

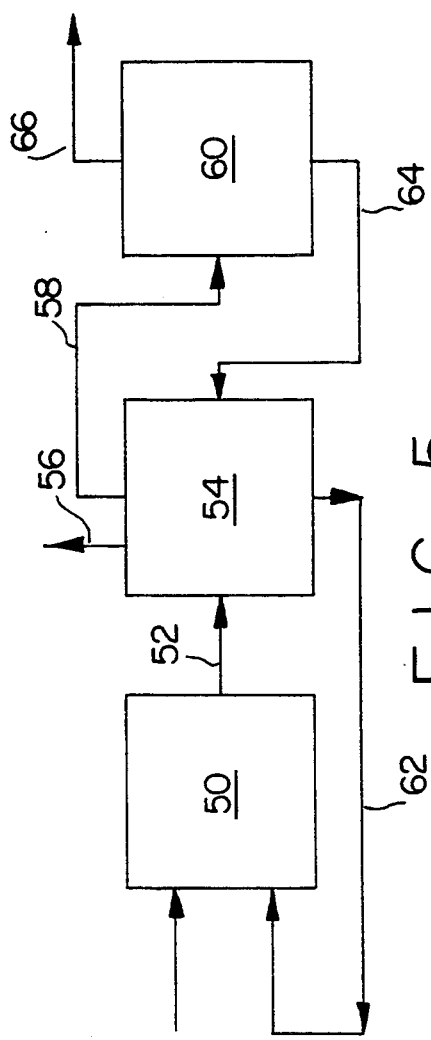
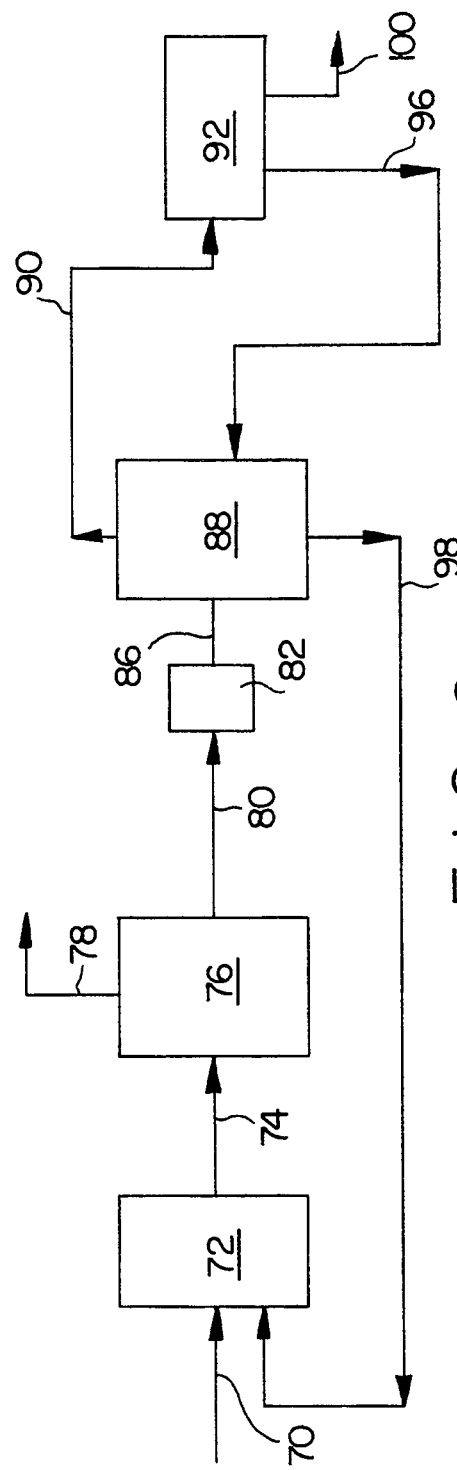

METHOD OF PRODUCING UNSATURATED HYDROCARBONS AND SEPARATING THE SAME FROM SATURATED HYDROCARBONS

RELATED APPLICATION

This application is a continuation-in part of Application Ser. No. 07/891,501, filed May 29, 1992, now abandoned.

1. TECHNICAL FIELD

The present invention is directed to a method of separating a saturated hydrocarbon from an ethylenically unsaturated hydrocarbon using a pressure swing adsorption system in which the unsaturated hydrocarbon is preferentially adsorbed under temperature and pressure conditions which minimize the loss of energy. The method produces a high purity stream of the ethylenically unsaturated hydrocarbon at less cost than prior systems. The invention is also directed to a method of producing ethylenically unsaturated hydrocarbons from saturated hydrocarbons which can meet various product requirements in an efficient manner by employing combined pressure swing adsorption systems as well as hybrid separation systems involving both pressure swing adsorption and distillation operations.

2. BACKGROUND OF THE PRIOR ART

It is known to separate saturated hydrocarbons (e.g. propane) from ethylenically unsaturated hydrocarbons (e.g. propylene) by distillation. The mixture of the saturated and unsaturated hydrocarbons is typically obtained from a dehydrogenator or hydrocarbon cracker. The cracker receives a feed gas composed primarily of the saturated hydrocarbon and dehydrogenates or cracks the feed gas to form the ethylenically unsaturated hydrocarbon in an admixture with residual unreacted feed gas.

The conventional method of producing propylene from a feed gas composed primarily of propane usually involves three principal steps:

i) the production of propylene from a propane feed in a dehydrogenator or hydrocarbon cracker.

ii) the separation of the light components, and iii) the separation of propylene from propane and other heavy components.

The production of propylene from propane is normally carried out in a catalytic dehydrogenation reactor or a thermal cracker. A catalytic dehydrogenator reactor is normally operated at high temperatures (500° to 700° C.) and low pressures (3 to 50 psia). The resulting effluent is cooled and compressed, and the light components such as hydrogen, methane and $C_2$ hydrocarbons are removed. $C_2$ components may be removed by a deethanizer; the aforementioned lighter components may be removed by a demethanizer. The heavier components ($C_3$'s and higher) are subsequently fed into a $C_3$-splitter, which typically is a 2-column distillation system. The first column of the 2-column distillation system separates a substantial portion of the propane to produce a chemical or refinery grade propylene of at least 90 volume percent purity, typically about 96 volume percent. The second column improves the purity level to 99+ volume percent to obtain polymer grade propylene. The heavier components are subsequently removed by a deoiler to reclaim the unreacted propane for recycling back to the reactor.

The process of separating propylene from propane by distillation is both difficult and costly. This is because the production of polymer grade propylene is a very energy-intensive process. Typically, the second distillation column must be nearly equal in size to the first distillation column, adding significant capital expense to the process. Further, the energy required to improve purity from 96 volume percent to 99+ volume percent in a conventional distillation process is more than half of that required to produce chemical or refinery grade purity propylene (about 96 volume percent purity) from a 40 volume percent propane/60 volume percent propylene feed mixture.

In a conventional process for producing propylene from propane, the feed mixture obtained from the reactor at low pressure (3 to 50 psia) and high temperature (500° to 700° C.) must be compressed to higher pressures, typically from 200 to 650 psia, and then cooled to near ambient temperatures (20° to 50° C.) in order to remove the light components. Demethanizer and deethanizer columns are normally used for the removal of the light hydrocarbon components. To separate propylene from propane using distillation columns (super-fractionators), the process gas stream may be expanded and cooled further to as low as −50° C.

A propane-rich stream is obtained as the bottom product of the super-fractionator, and this stream is recycled back to the reactor. A propylene-rich gas is obtained from the top of the column as the final product. If propylene purity levels exceeding 96 volume percent are desired, then a second distillation column must be used. Along with the high capital expense of the distillation columns, the increase in pressure and reduction in temperature of the reactor effluent requires a significant consumption of energy which adds to the cost of the system.

Thus, the employment of consecutive distillation columns for the production of an unsaturated hydrocarbon from a feed stream of a saturated hydrocarbon and for the separation of saturated and unsaturated hydrocarbons suffers from two principal disadvantages. The process uses large amounts of energy when the high temperature gas is compressed and cooled prior to entering the distillation system. In addition, a large capital expenditure is incurred when a plurality distillation columns are used to obtain unsaturated hydrocarbon purity levels up to and exceeding 99 volume percent, particularly in the production of propylene from propane.

U.S. Pat. No. 4,917,711 describes the adsorption of the unsaturated hydrocarbon from a mixture containing the unsaturated hydrocarbon and a saturated hydrocarbon using an adsorbent comprising a copper compound and a high surface area support such as silica gel, or zeolite molecular sieves, such as 4A, zeolite, 5A zeolite, type X zeolite or type Y zeolite.

SUMMARY OF THE INVENTION

In its broadest aspect, the invention is a method of separating gaseous saturated and gaseous unsaturated hydrocarbons by pressure swing adsorption at a temperature in the range of about 50° to about 200° C. using 4A zeolite as the adsorbent.

The present invention is most applicable to the separation of alkenes having 2 to 6 hydrocarbons from alkanes having 2 to 6 hydrocarbons, and is particularly applicable to the separation of one or more alkenes having 2 to 4 carbon atoms from one or more alkanes having 2 to 4 hydrocarbons by preferentially adsorbing the alkene(s) in a pressure swing adsorption process carried out alone, as described above, or carried out in combination with a distillation process or another pressure swing adsorption process, the particular system employed depending on the components present in the feed stream being treated and the specifications of the final product.

The present invention optionally utilizes hybrid process techniques to effectively meet more stringent product specifications. In one hybrid separation method for producing gaseous alkene in accordance with the invention, the gaseous mixture of an alkene and an alkene, such as a mixture of propylene and the corresponding alkane, propane, obtained from the dehydrogenation of a propane feed gas, is compressed and cooled to remove the light components, i.e. hydrocarbons having up to 2 carbon atoms, and then fed to a distillation column for further purification. Since a warm gaseous product is often desired, rather than using two serially-connected distillation columns to separate propane from propylene according to conventional procedures, the second distillation step can be replaced by the above-described pressure swing adsorption process.

The bottom product of the distillation column, a saturated hydrocarbon rich stream, is recycled to the reactor. The overhead product, an alkene-rich stream, is heated and sent to the above-described pressure swing adsorption system where most of the remaining alkane is removed by the preferential adsorption of the alkene. Any alkane remaining in the pressure swing adsorption unit can be recycled back to the dehydrogenation unit or to the distillation column as a mixture with the non-adsorbed alkene. A high purity alkene vapor (i.e. 99 or higher volume percent alkene) is obtained. Upon regeneration of the adsorbent in the pressure swing adsorption system, an unsaturated hydrocarbon is obtained at purity levels which can exceed 99 volume percent.

If a liquid alkene product is desired, the pressure swing adsorption process is carried out prior to the distillation step. In this embodiment, the gaseous mixture, which has been stripped of the light hydrocarbon components, is fed into the pressure swing adsorption unit where a major portion of the alkane is removed and recycled to the reactor. The alkene-rich stream from the pressure swing adsorption unit is then sent to a distillation column where most of the remaining alkane is removed. A liquid alkene product is obtained from the overhead condenser of the distillation column at purity levels which can well exceed 99 volume percent.

In another embodiment of the invention, the light components such as hydrogen, methane, $C_2$ hydrocarbons and, possibly some higher alkanes from the reactor effluent are removed by a preliminary first pressure swing adsorption process. In this embodiment, the stream exiting the preliminary pressure swing adsorption process is subjected to the above-described pressure swing adsorption process, wherein the alkane is separated and recycled to the reactor and a high purity stream of alkene is obtained as the final product. In this embodiment, very high purity liquid alkene can be obtained by adding a distillation step at the end of the second adsorption process.

BRIEF DESCRIPTION OF THE DRAWINGS

The following drawings are illustrative of embodiments of the invention and are not intended to limit the invention as encompassed by the claims forming part of the application.

FIG. 1 is a schematic view of one embodiment of the invention in which a mixture of saturated and unsaturated hydrocarbons is sent directly to a pressure swing adsorption system;

FIG. 2 is a schematic view of another embodiment of the invention, similar to FIG. 1, in which a purge gas is used to regenerate the pressure swing adsorption system;

FIG. 5 is a schematic view of another embodiment of the invention which is similar to that shown in FIG. 4, wherein the two pressure swing adsorption units are combined into a single pressure swing adsorption system; and FIG. 6 is a schematic view of another embodiment of the invention in which a mixture of saturated and unsaturated hydrocarbons is sent to a distillation column and an unsaturated hydrocarbon rich feed is sent to a pressure swing adsorption system for further purification.

DETAILED DESCRIPTION OF THE INVENTION

Figure 3:
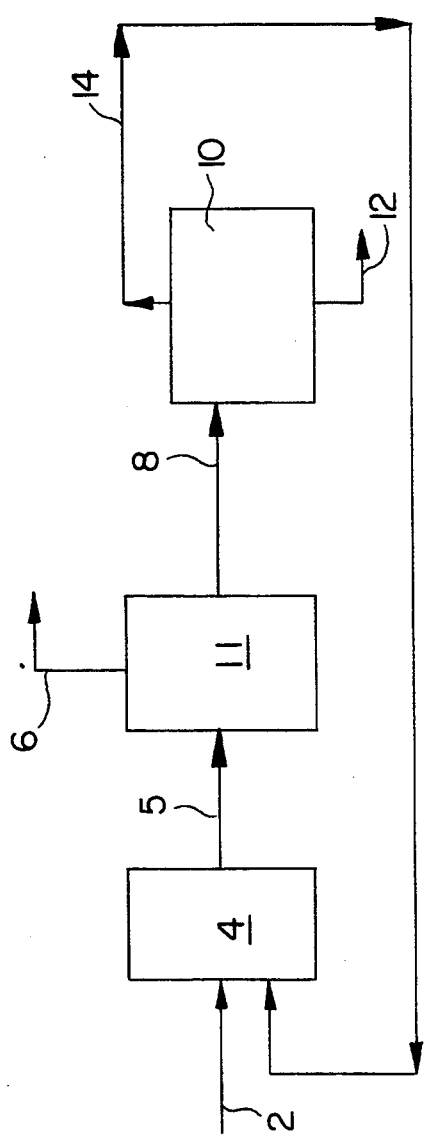
FIG. 3 is a schematic view of a further embodiment of the invention in which a first pressure swing adsorption unit treats the light components and a second pressure swing adsorption unit separates the saturated hydrocarbon from the unsaturated hydrocarbon.

The invention is useful for the separation of gaseous alkenes from gaseous alkanes. The separation is effected by pressure swing adsorption using an adsorbent which more readily adsorbs alkenes than alkanes at the adsorption temperatures employed. Alkenes which can be separated by the process of the invention are generally those having 2 to 6 carbon atoms and include ethylene, propylene, the butenes, the pentenes and the hexenes. The gaseous alkanes from which the alkenes are separated are those generally having 2 to 6 carbon atoms and include ethane, propane, the butanes, the pentanes and the hexanes. In a preferred embodiment the process of the invention is applied to the separation of alkenes having 2 to 4 carbon atoms from alkanes having 2 to 4 carbon atoms. The most beneficial application of the invention involves the separation of an alkene having 2 to 6 carbon atoms from the corresponding alkane, i.e. an alkane having the same number of carbon atoms as the alkene being separated. Preferred separations include ethylene-ethane separation, propylene-propane separation and separations between one of the butenes, e.g i-butylene, and one or more of the butanes, e.g. n-butane or i-butane.

A preferred adsorbent for the adsorption of the alkene from the alkene-alkane mixture is type 4A zeolite, i.e. the sodium form of type A zeolite, which has a pore size of about 4 Angstrom units. This adsorbent provides enhanced selectivity and capacity in adsorbing alkenes from alkene-alkane mixtures at elevated temperatures.

In some instances it may be desirable to exchange some of the sodium ions by other metal ions. This may be done, provided that the percentage of ions exchanged is not so great that the ability of the adsorbent to selectively adsorb alkenes from alkene-alkane gas mixtures at elevated temperatures is not significantly adversely affected. In general, it has been determined that up to about 25 percent of the sodium ions in 4A zeolite can be replaced by ion exchange with other cations without changing the 4A character of the adsorbent. Cations that may be ion exchanged with the 4A zeolite used in the alkene-alkane separation include, among others, potassium, calcium, magnesium, strontium, zinc, cobalt, silver, copper, manganese, cadmium, etc.

4A zeolite which contains certain oxidizable metal cations exhibits enhanced adsorptive capacity and selectivity with respect to the preferential adsorption of alkenes from gaseous alkene-alkane mixtures at temperatures above about 100° C. For instance, copper ion-exchanged 4A zeolite strongly adsorbs ehtylene and propylene from mixtures containing these alkenes and the corresponding alkanes at temperatures in the range of about 100° to 200° C.

The temperature at which the adsorption step of the alkene-alkane adsorption process is carried depends upon a number of factors, such as the particular alkene and alkane being separated, the particular adsorbent being used, e.g. unmodified 4A zeolite or a particular metal-exchanged 4A zeolite, and the pressure at which the adsorption is carried out. In general, the adsorption step is carried out at a minimum temperature of about 50° C. and preferably at a temperature of at least about 70° C. The upper temperature limit at which the adsorption step of the process of the invention is carried out is determined by mostly by economics. In general the adsorption step can be carried out at a temperature below the temperature at which the alkene undergoes chemical reaction, such as polymerization. When unmodified 4A zeolite is used as the adsorbent the reaction is generally carried out at or below 200° C., and is preferably carried out at a temperature at or below 170° C. When certain metal-exchanged 4A zeolites, particularly copper-containing 4A zeolite is used as the adsorbent the adsorption step is generally carried out at temperatures between about 100° C. and 200° C., and is preferably carried out at temperatures in the range of about 125° to 200° C. and is most preferably carried out at temperatures in the range of about 150° to about 200° C.

The pressures at which the adsorption and regeneration steps of the process of the invention are carried out are not critical, and in general, this step can be carried out at any of the usual pressures employed for gas pressure swing adsorption processes. Typically the absolute pressure during the adsorption step will range from about 0.2 to about 20 atmospheres absolute, and preferably from about 1 to 10 atmospheres, and during the regeneration step will range from about 20 millibars to about 1 atmosphere.

To simplify discussion of the invention, the preferred embodiments of the invention will be described with particular reference to propylene as the adsorbed alkene and propane as the nonadsorbed alkane. It should be understood, however, that the present invention is applicable to separation of other gaseous alkenes and alkanes, as detailed above.

Referring to the drawings and particularly to FIGS. 1 and 2, there is shown a first embodiment of the invention in which a gaseous mixture of propylene and propane is sent directly to a pressure swing adsorption system. As shown in FIGS. 1 and 2, a propane feed is sent via line 2 to a propane dehydrogenator or hydrocarbon cracker reactor 4 wherein a portion of the propane (typically about 40 percent by volume) is converted to propylene. The reaction is run under conditions typical in the art including a reaction temperature of 500° to 700° C. and a reaction pressure of 3 to 50 psia. The particular details of the dehydrogenation reaction are well known and form no part of the invention.

The mixture of propane and propylene is sent from dehydrogenator 4 via line 5 to a known device such as a demethanizer and deethanizer distillation column system 7 for removing substantially light components including $C_1$ and, where appropriate, $C_2$ hydrocarbons via line 6. The removal of the light components can also be carried out by the known method of compression and cooling.

The propane-propylene mixture, substantially devoid of light components, is sent via line 8 to pressure swing adsorption unit 10. Unit 10 has at least one bed containing 4A type zeolite adsorbent which is adapted to preferentially adsorb propylene while allowing propane to pass through the unit to be recycled with unrecovered propylene to dehydrogenator 4. Details of the construction and operation of pressure swing adsorption systems form no part of this invention, but such systems, including single and multiple beds are disclosed, for example, in U.S. Pat. Nos. 2,944,627 and 3,156,464.

A substantially pure (99+ volume percent) unsaturated hydrocarbon (propylene) stream exits unit 10 via line 12 to a storage vessel (not shown) or is sent directly to the end user such a polymerization reactor (not shown).

The propylene adsorbed by the adsorbent is removed through a typical regeneration process employed in pressure swing adsorption systems. The propylene adsorbed in the beds is removed by desorption, preferably under vacuum conditions, with a major portion being recovered through line 12 as product. A minor portion of the propylene is returned with the unreacted propane via line 14 to dehydrogenator 4 for further processing.

The adsorbent beds may be flushed with an inert purge gas such as nitrogen or a portion of the substantially pure unsaturated hydrocarbon product gas as shown specifically in FIG. 2. The purge gas mixture is then removed from pressure swing adsorption unit 10. If nitrogen is used as the purge gas, the resulting mixed stream is preferably combusted or vented to the atmosphere. Alternatively, a portion of the propane feed can be used as a purge gas via line 2 through line 15 in which case the off-gas is sent to the dehydrogenator 4. In addition, the product purity can be further improved by repressurizing the regenerated adsorbent bed with the unsaturated hydrocarbon product.

The propane feed is reacted in the dehydrogenator 4 at pressures generally in the range of from 3 to 50 psia and temperatures of 500° to 700° C. The resulting propane/propylene mixture, after removal of the light components, is sent to pressure swing adsorption unit 10, typically operating at a temperature of 50° to 200° C. and an absolute pressure of 1 to 10 atmospheres, as noted above. Thus, the operating temperature of pressure swing adsorption unit 10 is generally significantly higher than the operating temperature range of distillation columns in which the gaseous mixture must be cooled to temperatures as low −50° C. As a consequence, the embodiments of the present invention shown in FIGS. 1 and 2 are capable of separating saturated and unsaturated hydrocarbons with less cooling duty than is required in known distillation systems.

A preliminary pressure swing adsorption unit can be used to remove the light components as an alternative to a demethanizer/ deethanizer distillation system. Referring to FIG. 3, the mixture of propane and propylene is introduced into dehydrogenator 4 via line 2, and is discharged therefrom line 5 to preliminary pressure swing adsorption unit 11 which preferentially adsorbs propane and propylene; the light components including hydrogen, methane and C₂ hydrocarbons are consequently removed from the process stream through line 6. The adsorbents which are used in unit 11 to preferentially adsorb the propane and propylene and reject the light components are preferably selected from silica gel and activated carbon. The unreacted propane and the dehydrogenation product (propylene) leave pressure swing adsorption unit 11 via line 8 and enter second pressure swing adsorption unit 10. Alternatively, units 10 and 11 may be combined into a single system with separate beds for recovering the saturated and unsaturated hydrocarbons, and rejecting the light components. The propane-propylene mixture is treated in the same manner as described above in connection with the embodiments of FIGS. 1 and 2 to provide a substantially pure propylene product.

The embodiments shown and described in connection with FIGS. 1-3 are particularly adapted for the production of a gaseous unsaturated hydrocarbon such as gaseous propylene. In the embodiments which follow, a distillation column is added to the process scheme to provide options for the production of a liquid alkene product.

Figure 4:
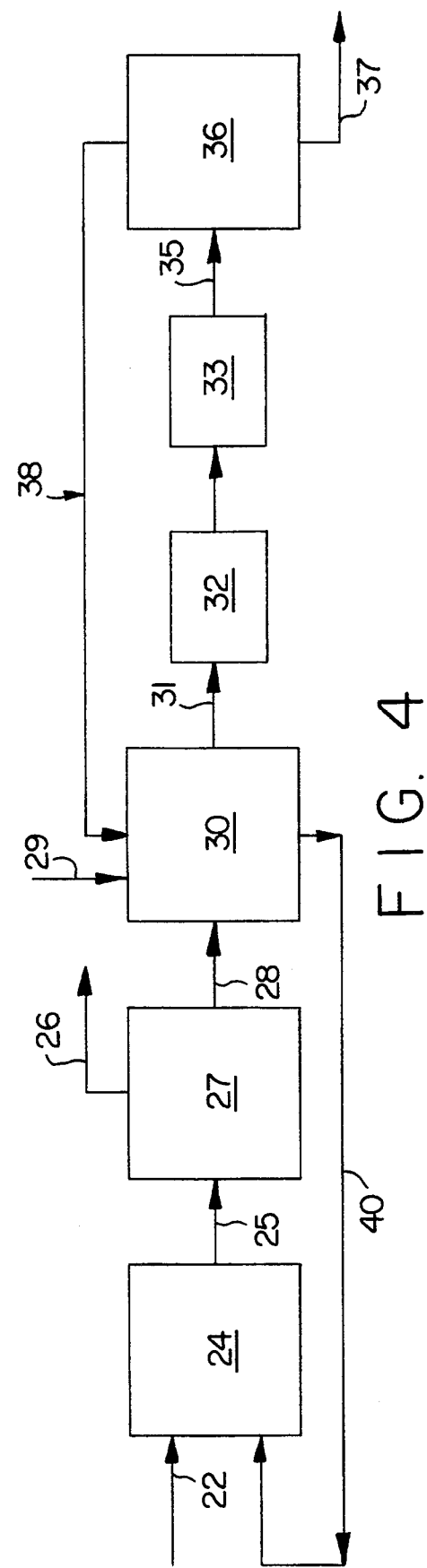
FIG. 4 is a schematic view of another embodiment of the invention in which the effluent of a dehydrogenation reactor is treated to remove light components in a first pressure swing adsorption unit and a mixture of saturated and unsaturated hydrocarbons is sent to a second pressure swing adsorption unit and the resulting unsaturated hydrocarbon rich feed is cooled, compressed, and sent to a distillation column for further purification.

Referring to FIG. 4, there is shown another embodiment of the invention in which a pressure swing adsorption system is first used to separate the alkene from a gas mixture to purity levels of about 96 volume percent. The alkene-rich stream is then sent to a distillation column to remove further amounts of alkene and thereby obtain the alkene at purity levels equal to or exceeding 99 volume percent.

The propane feed is sent via line 22 to dehydrogenator or thermal cracker 24 operating at a pressure of 3 to 50 psia and a temperature of 500° to 700° C. to form a mixture of propane and propylene in a ratio of about 40/60 volume percent as described in the embodiments of FIGS. 1-3. The mixture of propane and propylene may then be treated to remove the light components. This can be accomplished by compression and cooling, or by means of demethanizer and deethanizer columns, or, as shown specifically in FIG. 4, by using pressure swing adsorption unit 27. Unit 27 contains adsorbents such as silica gel and activated carbon which preferentially adsorb propane and propylene. The light components are then removed from unit 27 via line 26.

The gas mixture, now substantially devoid of the light components, proceeds via line 28 to second pressure swing adsorption unit 30 where the initial separation of propylene and propane occurs.

The propylene present in the propylene rich gas obtained from pressure swing adsorption unit 27 is adsorbed in second pressure swing adsorption unit 30, operating at temperature of 50° to 200° C. and an absolute pressure of about 1 to about lo atmospheres. The adsorbent beds of unit 30, preferably containing unmodified 4A zeolite, preferentially adsorb propylene to thereby produce a propylene product having a purity level of at least 90 volume percent, typically about 96 volume percent purity.

Pressure swing adsorption unit 30 may be purged with an inert gas such as nitrogen or propylene product gas via line 29. In the former embodiment, the purge gas mixture may be combusted or vented to the atmosphere. In the latter embodiment, the gaseous mixture is preferably recycled to pressure swing adsorption unit 30. The propane feed can be used as a purge gas as well by passing propane through line 29.

The resulting propylene-rich stream is removed from pressure swing adsorption unit 30 via line 31. This stream is compressed, for example, to 10 to 300 psig, by compressor 32 and the resulting compressed stream is cooled in heat exchanger 33 to a temperature of 40° to −50° C. The compressed and cooled gas is then sent via line 35 to distillation column 36. A mixture of propane and propylene is discharged from distillation column 36 and sent as a recycle back to pressure swing adsorption until 30 via line 38. A liquid propylene product having a purity level of 99+ volume percent is obtained as an overhead product via line 37. Since a substantial separation of the propylene and propane has been effected by pressure swing adsorption unit 30, the size of distillation column 36 as well as that of compressor 32 and heat exchanger 33 can be relatively small.

Referring to FIG. 5, there is shown an embodiment of the invention in which the pressure swing adsorption unit used to remove the light components from the mixed feed stream is combined with the pressure swing adsorption unit used to separate the alkene from the alkane to thereby form a consolidated pressure swing adsorption system. The propane-propylene mixed stream obtained from dehydrogenator 50 via line 52 is sent to combined pressure swing adsorption unit 54. Unit 54 has one set of adsorbent beds which preferentially adsorbs propane and propylene and rejects the light components, which are then removed from the system the line 56. The propylene-propane rich mixture, devoid of light components, is sent to a second set of adsorbent beds which preferentially adsorbs propylene to purity levels of up to 96 volume percent. The propylene rich stream is sent via line 58 to distillation column 60. Pressure swing adsorption unit 54 is purged to remove propylene and unreacted propane and the resulting gaseous mixture is recycled via line 62 to dehydrogenator 50 or vented to the atmosphere.

A bottom product is obtained from distillation column 60 which is composed primarily of unreacted propane and propylene. This mixed stream is recycled via line 64 to combined pressure swing adsorption unit 54. Substantially pure propylene (99+ volume percent) is removed from distillation column 60 via line 66.

Referring to FIG. 6, there is shown another embodiment of the invention in which a distillation column is first used to separate the unsaturated hydrocarbon from a saturated hydrocarbon to purity levels of about 96 volume percent. The unsaturated hydrocarbon rich stream is then sent to a pressure swing adsorption unit to remove further amounts of the alkane and thereby obtain the alkene at purity levels equal to or exceeding 99 volume percent.

The propane feed is sent via line 70 to dehydrogenator or thermal cracker 72 to form a mixture of propane and propylene in a ratio of about 40/60 volume percent as described in connection with the embodiments of FIGS. 1 and 2. The mixture leaves dehydrogenator 72 via line 74 at a pressure of 3 to 50 psia and a temperature of 500° to 700° C. The mixture is then treated to remove light components by cooling and compressing, by the use of demethanizer column 76, as shown specifically in FIG. 6 or by a pressure swing adsorption unit, as previously described. The light components are removed via line 78. After exiting demethanizer 76 via line 80, the gaseous mixture is cooled to a temperature of 40° to −50° C. in heat exchanger 82.

The cooled hydrocarbon mixture then proceeds via line 86 to distillation column 88 wherein the initial separation of propylene and propane occurs. A propylene-rich stream of at least 90 volume percent, typically about 96 volume percent purity is removed from distillation column 88 via line 90 for entry into pressure swing adsorption unit 92 for further purification. A recycle stream of propane and propylene is also sent from distillation column 88 to dehydrogenator 72 via line 98. A mixture of propane and propylene is recycled to distillation column 88 via line 96.

The propylene present in the propylene rich gas obtained from line 90 is adsorbed in pressure swing adsorption system 92 operating at a temperature of about 50° to about 200° C. and an absolute pressure of about 1 to about 10 atmospheres. The adsorbent beds, preferably containing unmodified 4A zeolite, preferentially adsorb propylene to thereby produce a propylene product having a purity level of 99+ volume percent which exits the system via line 100.

The adsorbent beds of the pressure swing adsorption system may be regenerated as described in connection with the description of the embodiment illustrated in FIGS. 1 and 2. An inert purge gas may also be provided. The purge gas is preferably a non-adsorbing gas such as methane or propane. When a purge gas is used the off gas will be sent directly to dehydrogenator 72. In the absence of a purge gas, a vacuum pump (not shown) may be used in a customary manner.

The invention is further illustrated in the following examples wherein, unless otherwise indicated, parts, percentages and ratios are on a volume basis.

EXAMPLES 1-8

These examples were carried out in a laboratory pressure swing adsorption apparatus comprising a pair of parallel-arranged stainless steel adsorption vessels each equipped with a heating jacket and containing 3842 grams (about 2.5 liters) of the indicated 4A type zeolite. The adsorption cycle consisted of the steps: bed equalization (9 secs.), countercurrent repressurization with nonadsorbed product (7 secs.), cocurrent adsorption of a feed gas (34 secs.), bed equalization (9 secs.), and countercurrent depressurization (41 secs.). The total time for a half-cycle was 50 secs. Each experiment was carried out for a minimum period of three hours, which ensured the existence of steady state conditions. The adsorption was carried out at a pressure of about 25 psia, the beds were equalized to a pressure of 10 psia, and the beds were evacuated to an absolute pressure of 100 to 200 millibars. In the examples a feed gas composed of about 12% propane and 88% propylene (by volume) was used as the feed gas. The flow rate of the feed stream, high pressure product (HPP) and low pressure product (LPP), which are determined for standard conditions, i.e. room temperature and atmospheric pressure, are reported in standard liters per minute (SLPM).

TABLE

| Ex. | Adsorbent | Temp. °C. | Flow Rate Feed | Flow Rate HPP | Flow Rate LPP | Propylene Recovered % | Propane Rejected % |
|---|---|---|---|---|---|---|---|
| 1 | 4A | 30 | 3.37 | 0.29 | 3.08 | 96.0 | 43.7 |
| 2 | 4A | 70 | 5.59 | 0.56 | 5.03 | 96.3 | 66.6 |
| 3 | 4A | 90 | 6.13 | 0.58 | 5.55 | 97.4 | 70.9 |
| 4 | 4A | 110 | 5.94 | 0.52 | 5.43 | 98.2 | 71.0 |
| 5 | 4A | 175 | 9.88 | 1.78 | 8.10 | 91.0 | 82.2 |
| 6 | 5A | 30 | 8.21 | 1.48 | 6.73 | 85.7 | 45.0 |
| 7 | 5A | 110 | 11.58 | 1.40 | 10.18 | 90.4 | 28.8 |
| 8 | 13X | 90 | 10.28 | 1.47 | 10.28 | 87.6 | 28.5 |

The above examples illustrate the benefits obtained by the invention. In the above series of examples, Examples 2-5 fall within the scope of the invention and Examples 1 and 6-8 are comparative examples. Examples 2-5 illustrate that when experiments within the scope of the invention were conducted a high percentage of the propylene in the feed stream was recovered, and good propane rejection rates were obtained. In comparison to this, Example 1 illustrates that when the adsorption process is practiced at 30° C., a high percentage of the propylene in the feed stream was recovered but only 43.7 percent of the propane in the feed stream was rejected (i.e. was in the nonadsorbed product stream).

Comparative Examples 6-8 show that 5A and 13X zeolites are much inferior to 4A zeolite for high temperature adsorptive separation of propylene and propane in that very poor propane rejection resulted from the use of these adsorbents.

The present invention is not limited to the foregoing examples and obvious variations of the invention apparent to those of ordinary skill in the art are included herein.

We claim:

1. A method of separating a gaseous alkene from a gas mixture comprised of said alkene and one or more alkanes comprising:
   (a) subjecting said gas mixture to a pressure swing adsorption process comprising passing said gas mixture through at least one bed of 4A zeolite adsorbent at a temperature above about 50° C., thereby preferentially adsorbing said alkene from said gas mixture; and
   (b) desorbing the adsorbed alkene from said at least one bed.

2. The method of claim 1, wherein said alkene contains 2 to 6 carbon atoms and said one or more alkanes contain 2 to 6 carbon atoms and said gas mixture is passed through said at least one bed of 4A zeolite at a temperature in the range of about 50° to about 200° C. and an absolute pressure of about 0.2 to 20 atmospheres.

3. The method of claim 2, wherein said alkene contains 2 to 4 carbon atoms and said one or more alkanes contain 2 to 4 carbon atoms.

4. The method of claim 1, wherein said alkene and at least one of said alkanes contain the same number of carbon atoms.

5. The method of claim 4, wherein said gas mixture consists substantially of propylene and propane.

6. The method of claim 4, wherein said gas mixture consists substantially of ethylene and ethane.

7. The method of claim 5 or claim 6, wherein said gas mixture is passed through said bed of 4A zeolite at a temperature in the range of about 70° to about 170° C. and an absolute pressure of about 1 to 10 atmospheres.

8. The method of claim 1, further comprising removing light components comprising hydrogen and alkanes having fewer carbon atoms than said alkene from said gas mixture prior to subjecting said gas mixture to said pressure swing adsorption process.

9. The method of claim 8, wherein the step of removing said light components from said gas mixture comprises subjecting said gas mixture to a preliminary pressure swing adsorption process prior to said pressure swing adsorption process, thereby preferentially adsorbing said alkene and alkanes other than those having fewer carbon atoms than said alkene from said gas mixture.

10. The method of claim 9, wherein said preliminary pressure swing adsorption process is conducted in the presence of at least one adsorbent selected from the group consisting of silica gel and activated carbon.

11. The method of claim 10 wherein said preliminary pressure swing adsorption process and said pressure swing adsorption process are carried out in a single pressure swing adsorption system having separate adsorbent beds.

12. The method of claim 1 further comprising fractionating the desorbate from said pressure swing adsorption process in a distillation column and removing a high purity alkene fraction as an overhead stream from said distillation column.

13. The method of claim 9 further comprising cooling the desorbate from said preliminary pressure swing adsorption process and distilling the cooled desorbate, thereby producing as the feed stream to said pressure swing adsorption process a gas mixture concentrated in said alkene.

14. The method of claim 13 further comprising the steps of dehydrogenating a feed stream comprised substantially of an alkane to form said gas mixture and recycling unreacted alkane from said pressure swing adsorption system to the unit in which said step of dehydrogenating the feed stream is carried out.

15. The method of claim 13 further comprising the steps of dehydrogenating a feed stream comprised substantially of an alkane to form said gas mixture, recycling unreacted alkane from said pressure swing adsorption process to the distillation column and recycling unreacted alkane from the distillation column to the unit in which said step of dehydrogenating the feed stream is carried out.

16. The method of claim 1 further comprising regenerating said at least one bed by vacuum means.

17. The method of claim 1 further comprising regenerating said at least one bed by purging with one or more of inert gas, nonadsorbed gas, and adsorbed product gas.

18. The method of claim 1 wherein said bed is regenerated by means of vacuum and purge during the regeneration step with one or more of an inert gas, nonadsorbed gas, and adsorbed product gas.

19. The method of claim 1 wherein said bed is repressurized with the adsorbed product gas.

20. The method of claim 1, wherein the adsorbent is copper-modified 4A zeolite and the adsorption step is carried out at a temperature above 100° C.

21. The method of claim 20, wherein the adsorption step is carried out at a temperature in the range of about 125° to 200° C.

22. The method of claim 20, wherein the adsorption step is carried out at a temperature in the range of about 150° to about 200° C.

* * * * *